United States Patent [19]
Kieturakis et al.

[11] Patent Number: 5,439,455
[45] Date of Patent: Aug. 8, 1995

[54] COMBINATION INTRODUCER CANNULA AND REDUCER FOR USE THEREIN

[75] Inventors: Maciei J. Kieturakis, San Carlos; Helmut L. Kayan, Redwood City, both of Calif.

[73] Assignee: General Surgical Innovations, Inc., Palo Alto, Calif.

[21] Appl. No.: 289,314

[22] Filed: Aug. 11, 1994

[51] Int. Cl.⁶ .............................................. A61M 5/00
[52] U.S. Cl. .................................... 604/264; 604/167; 604/247
[58] Field of Search ................ 604/264, 128, 167, 256; 128/3

[56] References Cited

U.S. PATENT DOCUMENTS

| | | | |
|---|---|---|---|
| 4,909,798 | 3/1990 | Fleischhacker et al. | 604/256 |
| 5,125,910 | 6/1992 | Freitas | 604/249 |
| 5,273,545 | 12/1993 | Hunt et al. | 604/167 |
| 5,284,475 | 2/1994 | Mackal | 604/247 |
| 5,350,362 | 9/1994 | Stouder, Jr. | 604/167 |

*Primary Examiner*—C. Fred Rosenbaum
*Assistant Examiner*—Michael L. Arness
*Attorney, Agent, or Firm*—Flehr, Hohbach, Test, Albritton & Herbert

[57] ABSTRACT

A combination of an introducer cannula and a removable reducer for use therewith. The introducer cannula comprises an elongate tubular member having proximal and distal extremities and having a flow passage extending therethrough. A housing is mounted on the distal extremity and has a chamber in communication with the flow passage in the tubular member. Proximal and distal spaced apart seals are disposed in the chamber and are carried by the housing. The reducer comprises a body having proximal and distal extremities. The body has a cylindrical extension and the cylindrical extension has at least two elongate slots formed therein which extend through the cylindrical extension from the proximal extremity to the distal extremity of the body. The elongate slots extend diametrically of the cylindrical extension and adjoin each other to provide a central opening. A membrane seal is carried by the body and overlies the central opening. The membrane seal has a hole therein in alignment with the central opening. The hole in the membrane has a diameter of less than the diameter of the central opening. The reducer is secured to the introducer cannula so that the cylindrical extension of the body of the reducer mates with the proximal seal of the introducer cannula.

9 Claims, 1 Drawing Sheet

COMBINATION INTRODUCER CANNULA AND REDUCER FOR USE THEREIN

This invention relates to the combination of an introducer cannula and a reducer and a reducer for use therein.

Cannulae used in laparoscopic surgery typically are two sizes, one of which is for passing tools for surgical or diagnostic purposes ranging from 10-12 millimeters in outside diameter and another size for graspers, shears and needle drivers and the like having an outside diameter of approximately 5 millimeters. Occasions often arise when it is desirable to utilize 5 millimeter instruments in the larger sized 10-12 millimeter inside diameter cannulae. However, in the construction of the larger size cannulae, the seals provided therein are incapable of forming good seals to prevent leaks around the 5 millimeter instruments after they have been inserted, particularly during laparoscopic procedures. In the past, attempts to overcome such leakage, reducers have been provided which often have been in the form of a housing extension which is provided with a smaller membrane seal for forming a seal around the smaller sized 5 millimeter instruments. However, in order to accommodate instruments having irregularly shaped external surfaces, particularly those which carry suture needles, there has been a need to provide such extension housings with a relatively large outside diameter to accommodate such irregularly shaped external surfaces and the curved suture needles. Such reducers have been cumbersome and difficult to use. In the past it has been the practice to remove a reducer from the cannula and then the small diameter grasper or other instrument is passed through the reducer membrane where the needle or suture is grasped after which the assembly is inserted into the cannula. This however is also objectionable because the reducer must be removed and inserted each time the suture needle is passed through the cannula. In addition, it has been found that in reducers having housings with large inside diameters, leakage can also occur when a small diameter tool is shifted to one side of the reducer extension housing. There is therefore a need for a new and improved introducer cannula and a reducer for use therewith which overcomes these disadvantages.

In general, it is an object of the present invention to provide a combination of an introducer cannula and a reducer for use therein which makes it possible to introduce instruments of greatly different diameters while retaining fluid-tight seals with respect thereto.

Another object of the invention is to provide a reducer of the above character which is relatively small and compact.

Another object of the invention is to provide a reducer of the above character which can be readily inserted and removed from the cannula.

Another object of the invention is to provide a reducer of the above character which makes it possible to pass a curved suture needle without the necessity of removing the reducer from the cannula.

Another object of the invention is to provide a reducer of the above character through which instruments or tools of irregular external shapes can be passed.

Another object of the invention is to provide a reducer of the above character for use therewith which makes it possible to pass instruments having irregular surfaces and curved suture needles while still retaining the instrument in a generally central position with respect to the reducer.

Another object of the invention is to provide a reducer of the above character which is relatively compact and which is inexpensive to fabricate.

Additional objects and features of the invention will appear from the following description in which the preferred embodiments are set forth in detail in conjunction with the accompanying drawings.

Figure 1:
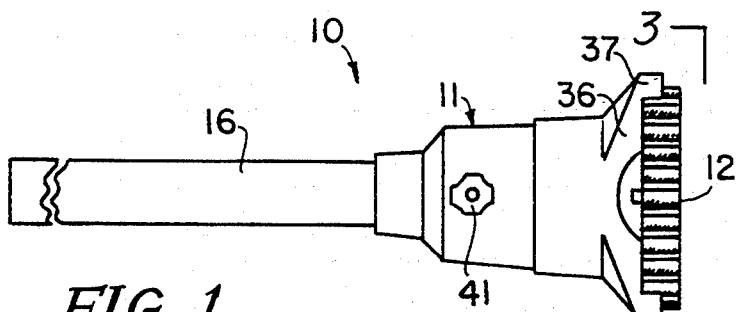
FIG. 1 is a side elevational view of the combination of an introducer cannula and the reducer for use therewith in which the reducer is mounted on the introducer cannula.
Figure 2:
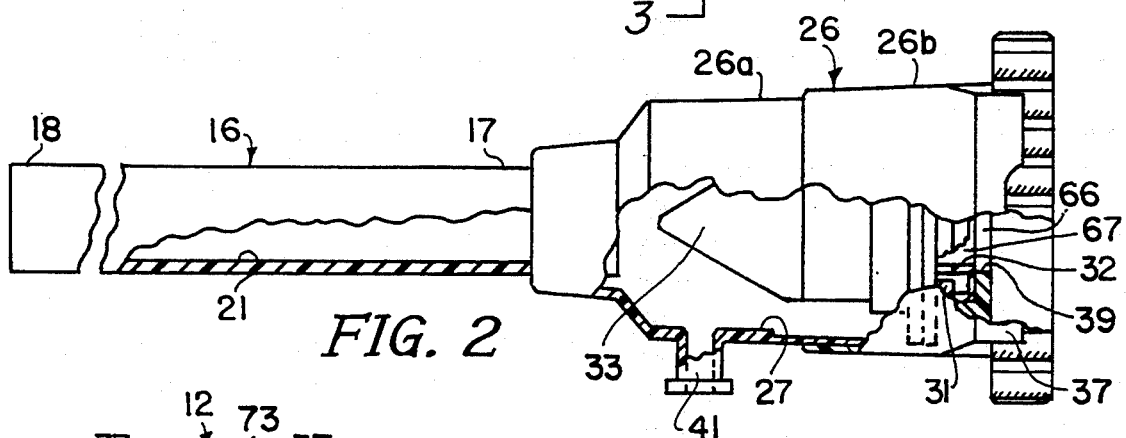
FIG. 2 is an enlarged side elevational view similar to that shown in FIG. 1 rotated by 90° from that shown in FIG. 1 and showing certain portions thereof in section.
Figure 3:
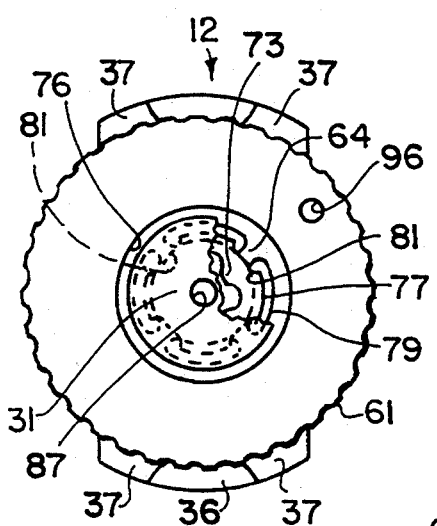
FIG. 3 is an enlarged end elevational view looking along the line 3—3 of FIG. 1 with certain parts broken away.
Figure 4:
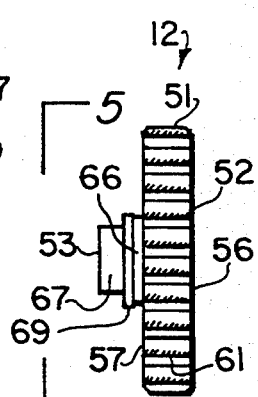
FIG. 4 is a side elevational view of the reducer shown in FIGS. 1-3.

The combination of an introducer cannula and a reducer is for use in surgical procedures for introducing instruments of greatly differing diameters into a body cavity. The cannula is comprised of an elongate tubular member having proximal and distal extremities and having a flow passage extending from the proximal to the distal extremity. A housing is mounted on the proximal extremity of the elongate tubular member and has a chamber therein in communication with the flow passage and the tubular member. Proximal and distal spaced apart seals are disposed in the chamber in the housing. The reducer is adapted to mate with the housing and be retained on the housing. The reducer is provided with a cylindrical extension which is adapted to form a sealing engagement with the proximal seal in the housing. A membrane seal is provided as part of the reducer and is disposed proximally of the cylindrical extension. The cylindrical extension is provided with a central opening extending therethrough. The cylindrical extension is provided with at least two elongate recesses therein which extend into the hole and extend through the extension in the same direction as the hole.

More particularly as shown in the drawings, the combination 10 is comprised of an introducer cannula 11 and a reducer 12. The introducer cannula 11 is of a conventional type and consists of an elongate tubular member 16 formed of a suitable material such as surgical grade plastic with proximal and distal extremities 17 and 18. The tubular member 16 has a wall thickness sufficient to provide rigidity so that it can be introduced through a skin seal (not shown) typically utilized in laparoscopic surgical procedures to obtain access to a cavity within a body as for example in a human body.

The elongate tubular member has a suitable length as for example 10 centimeters and has a wall thickness of 0.014" to provide a bore or flow passage 21 extending therethrough having an inside diameter which is great enough as for example 12 millimeters to accommodate surgical instruments having an outside diameter ranging from 10-11 millimeters.

A housing 26 is mounted on the proximal extremity 17 of the tubular member 16. The housing 26 is formed of a medical grade plastic and is formed in two parts 26a and 26b which form a generally cylindrical chamber 27 therein. Proximal and distal seals 31 and 32 are provided in the chamber 27 and are carried by the housing 26 The seal 31 is a conventional membrane type seal formed of elastomeric material which is carried by the housing 26 and has a hole 32 of a size of 8–9 millimeters therein. The second seal or distal seal 33 is in the form of a conventional duck bill valve which is also carried by the housing 26.

The housing 26 is provided with an outwardly extending flange 36 which is provided with proximally extending spaced-apart lips 37 which are adapted to guide the reducer 12. The flange 36 is also provided with a circular recess or hole 39 which is adapted to cooperate with the reducer 12 as hereinafter described.

The housing 26 is provided with a conventional Luer-type fitting 41 through which gas can be introduced through the introducer cannula 11.

Figure 5:
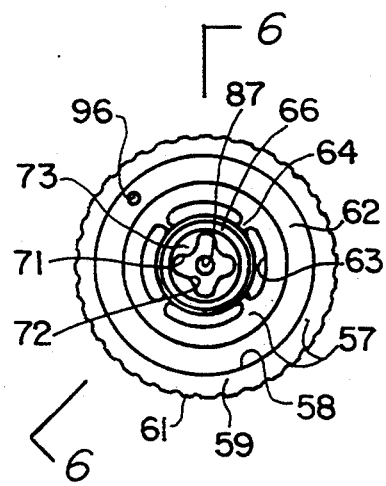
FIG. 5 is an elevational view looking along the line 5—5 of FIG. 4.
Figure 6:
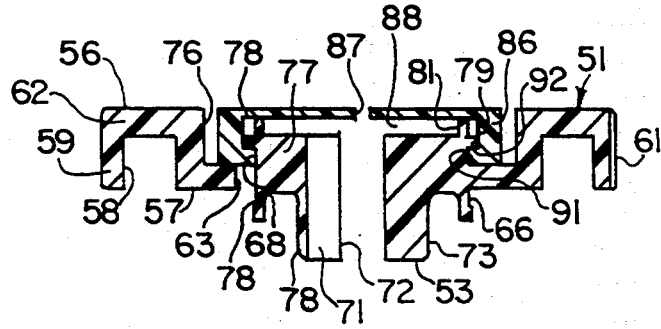
FIG. 6 is an enlarged cross-sectional view taken along the line 6—6 of FIG. 5.

The reducer 12 consists of a body 51 formed of a suitable medical grade plastic. The body 51 has a general cylindrical configuration and is provided with proximal and distal extremities 52 and 53 with a longitudinal axis extending therebetween. The body 51 is provided with a planar proximal wall 56 and a planar distal wall 57 which is planar and parallel to the proximal wall 56. An annular recess 58 is formed in the distal wall 57 to form a depending flange 59 which is provided with a serrated outer surface 61 adapted to be engaged by the fingers of the hand. The remaining central cylindrical portion 62 has a plurality of circumferentially spaced apart arcuate recesses 63 formed thereon as shown in FIG. 5 which are to provide intervening ribs 64. The ribs 64 adjoin a first cylindrical extension 66 which is centrally disposed and longitudinally aligned with the longitudinal axis of the body 51.

A second cylindrical extension 67 protrudes distally from the first cylindrical extension 66 and has a smaller diameter than the first cylindrical extension. The distal end of the first cylindrical extension 66 has an outwardly extending lip 68 (0.002") which is sized so that it can make a snap friction fit within the circular recess or hole 39 provided in the introducer cannula 11. The second cylindrical extension 67 is sized so that it can seat within the proximal seal 31 and form a sealing engagement therewith. An annular recess 69 is formed in the cylindrical extension 66 and opens distally therefrom.

The first and second cylindrical extensions 66 and 67 have at least two elongate slots 71 formed therein and as shown can have four elongate slots which extend radially of the cylindrical extensions 66 and 67. The elongate slots 71 extend longitudinally through the cylindrical extensions 66 and 67. They also extend outwardly to near the outer margin of the second cylindrical extension 67 but so that there remains at least a wall thickness of 0.005". They also extend inwardly to adjoin each other so that there is provided a central opening 72 which is defined by radially extending lobes 73 extending between the elongate slots 71. By way of example, with the second cylindrical extension 67 having a diameter of 10 millimeters, the slots can have a length of 4.5 millimeters and can have a suitable width as for example 3 millimeters to provide a central opening 72 of approximately 5 millimeters.

The body 51 has an annular recess 76 extending through the proximal surface 56 to form a cylindrical protrusion 77 which has a height which is so that its proximal surface 78 is spaced distally from the surface 56 for a small amount as for example 1 to 3 mils. An outer annular groove 79 is provided on the cylindrical protrusion 77 which opens sidewise of the protrusion 77 and through the surface 78. The cylindrical protrusion 77 has a centrally aligned recess 81 opening through the surface 78.

A cup-shaped membrane 86 formed of a suitable elastomeric material is disposed in the annular recess 76 and extends over the top of the cylindrical protrusion 77 to form a fluid tight seal with the annular surface 78. The cup-shaped membrane 86 can have a suitable thickness as for example 0.022" so that its outer surface is generally flush with the planar surface 56. The cup-shaped membrane 86 frictionally engages the cylindrical protrusion 77. The membrane 86 is provided with a centrally disposed opening or hole 87 which is of suitable size, as for example 3 millimeters which opens into a chamber 88 within the recess 81 and underlying the membrane 86. The cup-shaped membrane 86 is provided with an inwardly extending lip 91 seated within an annular recess 92 in the cylindrical protrusion 77 and serves to retain the cup-shaped membrane 86 in engagement with the cylindrical protrusion.

A hole 96 is provided in the body 51 which extends through the surface 56 into the annular recess 58 and is provided for attaching a tether (not shown) when a tether is desired.

Operation and use of the combination of the introducer cannula 11 and the reducer 12 may now be described briefly as follows. Let it be assumed that it is desirable to perform a laparoscopic surgery procedure in which one or more introducer cannulae are to be utilized in conjunction therewith. In such a procedure typically an incision is made in the skin of the patient, as for example in the abdominal wall. A skin seal (not shown) is positioned in the incision. Thereafter, an introducer cannula 11 of the type hereinbefore described is inserted through the skin seal to obtain access to a cavity in the body in which the incision has been made. Let it be assumed that the cannula is of the 10–11 millimeter size which is used for the larger surgical instruments for making a diagnosis or performing a surgical procedure that has been completed. Let it be assumed that it is desired to utilize the same introducer cannula for a smaller sized surgical device as for example a 5 millimeter device or tool, such as a grasper.

If it is assumed that it is desired to utilize such a 5 millimeter device, a reducer 12 of the present invention can be picked up and engaged by the hands of the surgeon doing the procedure and frictionally positioned within the flanges 36 provided on the housing 26 of the introducer cannula 11. As the reducer 12 is being inserted, the first cylindrical extension 66 will enter the first or proximal membrane seal 31 provided in the introducer cannula 12 form a sealing engagement therewith. Movement of the reducer 12 is continued inwardly until the first cylindrical extension 66 mates with and forms a frictional engagement in the circular hole 39 provided in the cannula 11. The frictional engagement between the first and second cylindrical recesses in the cannula 11 by the snap friction fit within the hole 39 and with the membrane seal 31 serves to frictionally retain the reducer in the introducer cannula 11.

As soon as the reducer 12 is in place, the five millimeter surgical device, as for example a grasper, can be inserted through the hole 82 in the membrane seal 81 to establish a fluid tight seal with the grasper. The surgical device or grasper can then be passed through the hole or central opening 72 of the reducer 12 and thence through the distal seal 32 in the introducer cannula 11 and through the bore 21 into the cavity into which the introducer cannula 11 has been placed. The central opening 72 formed by the star-like or cloverleaf-like configuration of the lobes 73 serves to support the surgical instrument in a generally central position so that a good fluid tight seal can be retained with respect to the membrane seal 81.

The elongate slots 71 between the lobes 73 serve to provide means whereby surgical instruments having irregular outer shapes can be passed through the reducer 12. In addition, the sizing of the elongate slots 71 is such that they can accommodate conventional curved surgical needles carried by the grasper which can be introduced through the hole 82 in the membrane 81 and thence into two diametrically opposed slots 71. The surgical needle can then be passed through the distal seal 32 and through the bore 21 into the body cavity to thereafter permit a conventional suturing operation to take place. A curved suture needle can be passed through the membrane 81 grasping the suture near the needle and dragging the needle through the hole 82 and then dragging it through the slots 71. The suture needle can be removed in a similar manner by merely withdrawing it through the slots 71 and then through the membrane seal 81.

With such a reducer it can be seen that repeated suturing can be readily performed without removing the reducer 12 from the introducer cannula 11.

In connection with the present invention it can be seen that where curved suture needles are to be passed through the reducer, it is necessary that the two opposed slots 71 have an overall combined length which is at least as great as the curvature of the surgical needle to permit the surgical needle to pass therethrough. This diameter is represented by the outer margins defining the slots 71 which by way of example can be in the vicinity of 9 millimeters. The smaller or lesser diameter provided by the outer radial surfaces of the lobes 73 such as 6 millimeters to retain the surgical instrument centered within the reducer 12. The proximal and distal extremities of the lobes 73 defining the slots 71 can be rounded to facilitate entry of the curved surgical needles into the slots during insertion and withdrawal of the surgical needles.

In connection with the reducer 12 of the present invention it can be seen that the width of each elongate slot must be less than the diameter of the instrument to be centered thereby but should be wide enough to pass a surgical needle therethrough. Thus for a 5 millimeter surgical instrument the slots should have a width less than 5 millimeters and for a surgical needle having a diameter and thickness, as for example 0.5 mm., the width of the slots should be greater than that to permit the needle to pass therethrough.

Thus it can be seen that by a judicious choice of dimensions for the slots 71, a wide variety of surgical instruments and needles can be accommodated.

It can be seen that the reducer of the present invention is particularly efficacious because it is compact and short in length and can be readily retained by a conventional introducer cannula. It is very compact but still serves the important functions of providing an excellent seal with smaller surgical instruments while retaining the same in a generally central position to insure that a good fluid tight seal is retained while also giving it the capability of passing surgical instruments therethrough having irregular surfaces. Also it is possible to introduce and remove surgical needles without the necessity of removing the reducer from the introducer cannula.

Although the introducer cannula and the reducer have been described as being formed of a plastic such as a polycarbonate or polysulfone, other materials such as metal can be used if desired. Elastomeric material utilized for the seals can be in the form of silicon rubber or Kraton.

In view of the foregoing, it can be seen that there has been provided the combination of an introducer cannula and a reducer and a reducer for use therewith which makes it possible to utilize surgical instruments of greatly varying diameters, as for example large diameter surgical instruments having a diameter of 10–11 millimeters and smaller surgical instruments having a diameter of 5 millimeters. The reducer utilized is small and compact and can be manufactured inexpensively.

What is claimed is:

1. A combination of an introducer cannula and a removable reducer for use therewith, the introducer cannula comprising an elongate tubular member having proximal and distal extremities and having a flow passage extending therethrough, a housing mounted on the distal extremity and having a chamber in communication with the flow passage in the tubular member, proximal and distal spaced apart seals are disposed in the chamber and carried by the housing, the reducer comprising a body having proximal and distal extremities, the body having a cylindrical extension having a central opening therein, the cylindrical extension having at least two elongate slots formed therein and extending through the cylindrical extension from the proximal extremity to the distal extremity of the body, said elongate slots extending diametrically of the cylindrical extension and opening into the central opening, a membrane seal carried by the body and overlying the central opening, said membrane seal having a hole therein in alignment with the central opening, said hole in the membrane having a diameter of less than the diameter of the central opening and means carried by the body and by the introducer cannula for securing the reducer to the introducer cannula so that the cylindrical extension of the body of the reducer mates with the proximal seal of the introducer cannula.

2. A combination as in claim 1 wherein the cylindrical extension of the body of the reducer is provided with four diametrically extending slots.

3. A combination as in claim 1 wherein the reducer is to be utilized with a surgical instrument having a predetermined diameter, said slots having a width of less than the predetermined diameter of the surgical instrument, said central opening having a diameter at least slightly greater than the diameter of the predetermined diameter of the surgical instrument.

4. A combination as in claim 3 wherein the bore in the cannula has a diameter of approximately 10–12 millimeters and wherein said central opening has a diameter of approximately 5–7 millimeters.

5. A combination as in claim 1 wherein said reducer is frictionally retained in said housing.

6. A reducer for use with an introducer cannula to make it possible to utilize the introducer cannula for a larger diameter surgical instrument and for a smaller diameter surgical instrument comprising a body, said body having a cylindrical extension, the cylindrical extension having at least two diametrically extending slots formed in the cylindrical extension and extending from the proximal extremity to the distal extremity of the body and adjoining each other to form a centrally disposed opening therebetween, said opening having a diameter which is slightly greater than the diameter of the surgical instrument and said slots having a width which is less than the diameter of the surgical instrument and an elastomeric membrane type seal carried by the body and overlying the central opening, said seal having a hole therein which has a diameter slightly less than the diameter of the central opening.

7. A reducer as in claim 6 wherein said cylindrical extension is provided with four of said elongate slots.

8. A reducer as in claim 7 wherein said slots have a width less than the diameter of the opening.

9. A reducer as in claim 8 wherein said opening has a diameter less than the diameter of the larger diameter surgical instruments.

* * * * *